United States Patent [19]

Plessers et al.

[11] Patent Number: 4,557,152
[45] Date of Patent: Dec. 10, 1985

[54] SAMPLING DEVICE FOR MOLTEN METALS

[75] Inventors: Jacques J. Plessers, Houthalen; Alfons L. Theuwis, Zonhoven, both of Belgium

[73] Assignee: Electro-Nite Co., Philadelphia, Pa.

[21] Appl. No.: 536,594

[22] Filed: Sep. 26, 1983

[30] Foreign Application Priority Data

Sep. 29, 1982 [BE] Belgium ............... 2/59850
Jul. 19, 1983 [BE] Belgium ............... 2/60164

[51] Int. Cl.⁴ .............................. G01N 1/12
[52] U.S. Cl. ..................... 73/864.55; 73/DIG. 9
[58] Field of Search ............ 73/864.53–864.59, 73/DIG. 9

[56] References Cited

U.S. PATENT DOCUMENTS

| | | | |
|---|---|---|---|
| 3,455,164 | 7/1969 | Boyle | 73/354 |
| 3,646,816 | 3/1972 | Hance et al. | 73/DIG. 9 |
| 4,102,197 | 7/1978 | Bardenheuer et al. | 73/354 |
| 4,197,745 | 4/1980 | Kumbrant | 73/425.4 R |
| 4,212,203 | 7/1980 | Falk | 73/864.55 |
| 4,361,053 | 11/1982 | Jones et al. | 73/864.53 |

FOREIGN PATENT DOCUMENTS 1526144  5/1968  France .

Primary Examiner—Charles Hart
Attorney, Agent, or Firm—Seidel, Gonda, Goldhammer & Abbott

[57] ABSTRACT

A sampling device for liquid metals contains a pipe (5) and a head (1) fixed on an end thereof, wherein a sampling chamber (11) is formed, which head (1) contains a part (2) of fireproof material which partially limits the sampling chamber (11), which is provided with a supply orifice (12,46) to the sampling chamber and which is put in the pipe (5) with a narrow end (3) in such a way that the sampling chamber (11) is located entirely outside of the pipe (5). The device also has at least one small cooling plate (9) forming at least a part of the well of the sampling chamber (11) and thus also limits the sampling chamber. The part (2) is made of a material that at least during the sampling offers a structure letting gas pass.

20 Claims, 12 Drawing Figures

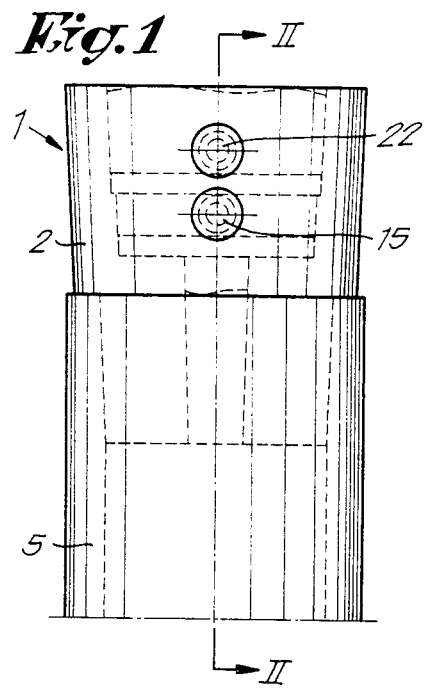
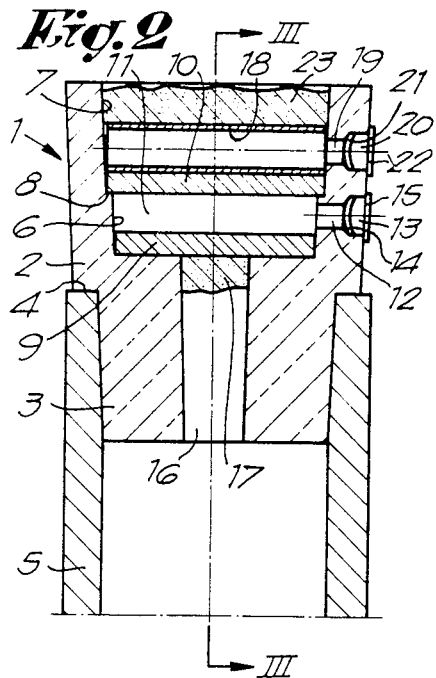
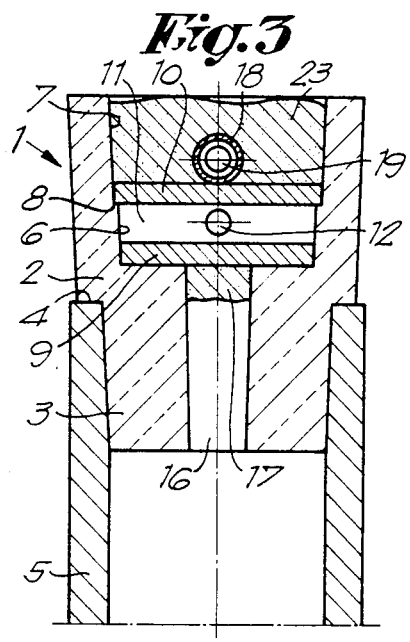
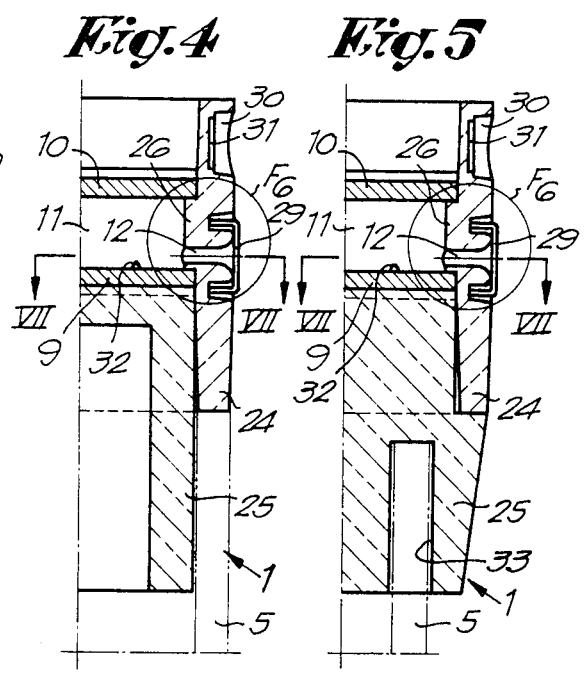

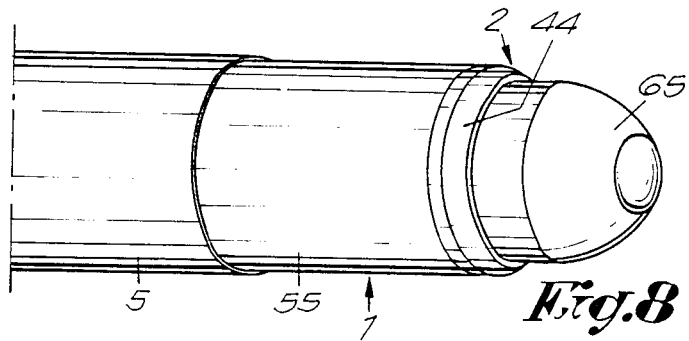
Fig.8
Fig.6
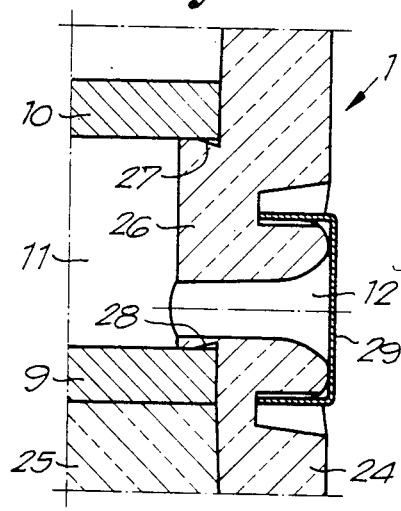
Fig.11
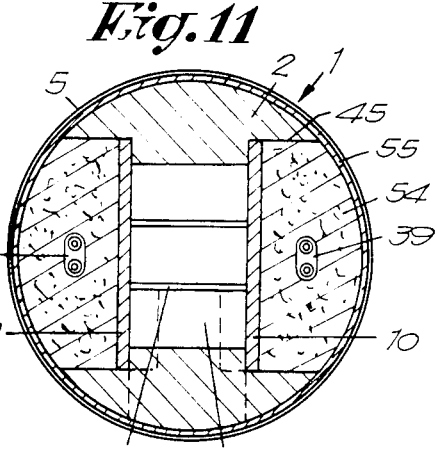
Fig.7
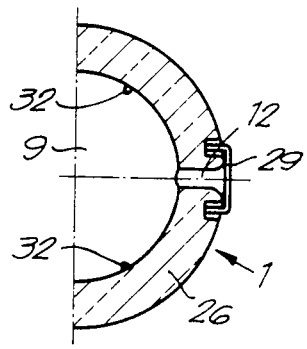
Fig.12
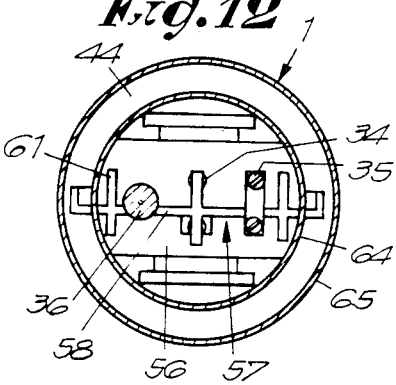

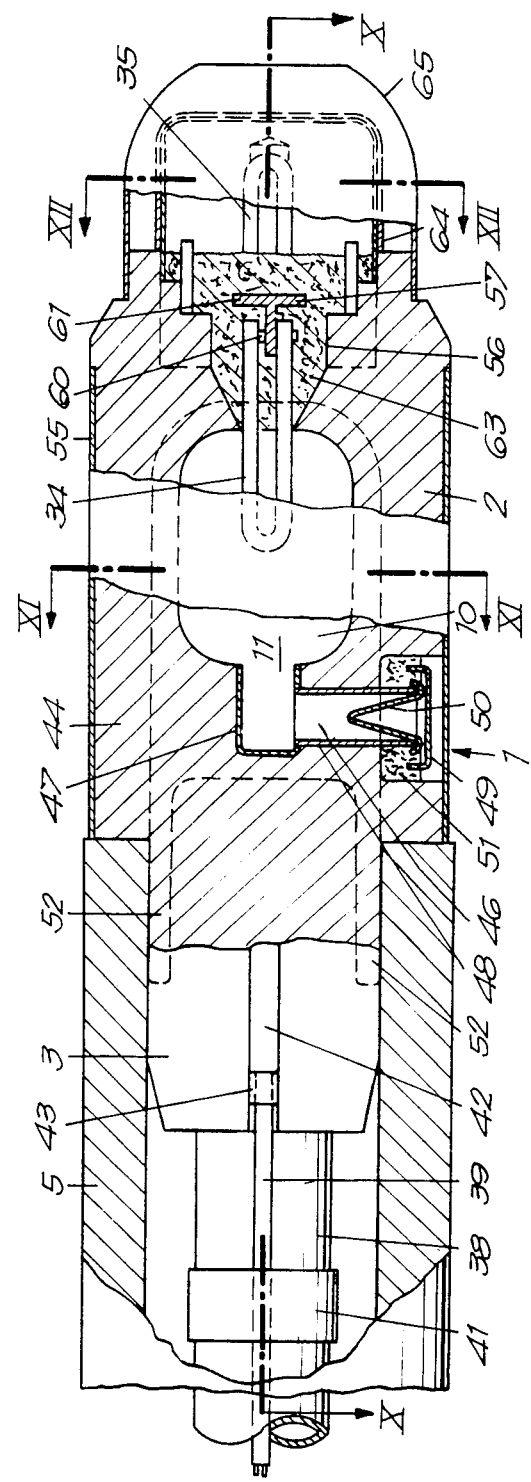

SAMPLING DEVICE FOR MOLTEN METALS

The present invention relates to a sampling device for molten metals comprising a tube and of a head fixed on an extremity of the tube wherein a sample chamber is formed. This head contains a body of fire-proof material partially limiting the sampling chamber and is provided with an inlet aperture to the sampling chamber. The hand is connected with the aforesaid tube in such a way that the sampling chamber is located completely outside of the pipe. At least one little cooling plate, forms at least one part of the wall of the sampling chamber and thus also limits the sampling chamber.

A sampling device of this kind is known from the French Pat. No. 1,526,144. In this known device, the body is made of ceramic material and thus of a material impervious to gas. The device contains only one cooling component in the shape of a little metallic disc, which is located in the sampling chamber, for instance against the inside of the chamber.

Due to the fact that the body is made of costly ceramic material, the device is relative expensive. Furthermore, due to the heavy mass of ceramic material, the liquid metal in the sampling chamber may cool down too rapidly, whereby it may be difficult to measure the solidifying point of the metal.

Due to the fact that the sampling chamber is limited on all sides by material not letting gas to pass, special provisions must be taken in order to allow gas to escape from the sampling chamber during the sampling of the sample. These provisions are formed by a canal which extends centrally through the wall of the sampling chamber and exits into the aforesaid pipe.

The presence of this canal makes the manufacturing of the body difficult. In order to prevent liquid metal discharge into the pipe, this canal must be relatively long and thus the wall of the body located at the side of the pipe must be relatively thick, which also negatively influences the cost price of the head.

Furthermore, the escape of gas towards the pipe takes place in a chamber wherein there is already air dilatating through warming up. The canal can also be completely or partially obstructed. It is thus possible that the evacuation of air or gas is insufficient and there is a risk that the sampling chamber does not become completely filled or that the sample contains gas inclusions. The hot air and gases which arrive into the pipe can also cause damage in this pipe to the electric circuits which extend throughout this pipe when the sampling device contains measuring electrodes which are mounted in or on the head.

The purpose of the invention is to remedy the aforesaid and other drawbacks and to provide a sampling device which is simple of construction, relatively cheap and allows a sample to completely fill the sampling chamber and does not contain gas or air inclusions. During the sampling operation air and gases escape through the body without getting into the pipe.

Fit for the purpose is the body made from agglutinated sand. A sampling device with a head the body of which is made from agglutinated sand is known in itself from the U.S. Pat. No. 3,455,164.

That device, however, is not of the kind intended here, in view of the fact that the sampling chamber is not limited partially by the body and partially by a cooling component.

For in all forms, one excepted, of the sampling device according to the U.S. Pat. No. 3,455,161 the sampling chamber is completely limited by agglomerated sand. So no cooling component is mounted in the sampling chamber.

Furthermore, the sampling chamber is completely located in the pipe. Air and gases during the sampling chamber get mainly into the pipe. Due to the fact that this pipe also completely encircles the sampling chamber, it must have a relatively great diameter, due to which this pipe is relatively expensive and heavy. Furthermore, the removal of the sample from the sampling chamber requires that one should disconnect the head from the pipe, which is not easy to do.

The removal of the sample would be considerably simpler if the sampling chamber would be located entirely outside of the pipe. It would then be easy to smash the part of the head which is located outside of the pipe to liberate the sample. It was, however, currently thought that, when the body is made of agglomerated sand or of another material with a structure pervious to gas, the head may extend outside of the pipe only in a limited proportion and that certainly the part of the head which encircles the sampling chamber and is relatively thin should be located in the pipe. As was expressly mentioned in the last named U.S. patent, one was of the opinion that the agglomerated sand looses its strength due to the heat of the molten metal, because of the binding agent burning.

Now, the applicant has surprisingly discovered that in the case wherein the sampling chamber is limited by one or more little cooling plates, the sampling chamber, also when the body is made of a material pervious to gas and in particular of agglomerated sand, may nevertheless be located entirely outside of the pipe. The head keeps its strength a sufficiently long time to allow one to take a sample.

In the form of execution according to FIG. 5 of the U.S. Pat. No. 3,455,164 the sampling chamber is partially located outside of the pipe, but not entirely. Furthermore, the sampling chamber is nearly completely limited by a little pipe made of quartz and the body of agglomerated sand only forms the envelope of the aforesaid little pipe made of quartz. Nearly all of the air and gases which when the liquid metal penetrates escape from the sampling chamber will find their way into the pipe.

According to the invention, the body of the head may be made as well of one piece as of many pieces. In a noteworthy embodiment of the invention, the cooling component closes an orifice in the body, the orifice opening on the sampling chamber and on the outside of the part of the body which is located outside of the pipe. In this embodiment, the cooling component may be applied after the shaping of the body and fixed on the same, for instance by means of fireproof cement. This makes the manufacture easier, especially when the body is made of only one piece.

In a further embodiment, the feed opening will be made so that a closing cap may be provided for, which is located inside of the outer wall of the aforesaid head body.

Another characteristic of the invention is a butt joint for the cooling components, which limits the sampling chamber on the upper side and on the under side, which are made partly conically in order to prevent the formation of burrs, principally burrs perpendicular to the plane of the sample. Preferably, the sampling chamber shall be provided with marks, for instance with protrusions, in order to clearly mark on the sample how it has been taken.

In another embodiment of the invention the head is provided with an armature. This armature preferably extends into the part of the head which is located in the aforesaid pipe. Suitably the armature forms a whole with the cooling component. When the cooling component closes an orifice in the body which opens into the sampling chamber and on the outside of the part of the body located on the outside of the pipe, this armature can extend along the body, for instance in a groove thereof and, for instance, be assembled to the body by fireproof cement.

In a preferred embodiment of the invention the sampling device contains at least two measuring components of the group formed by thermocouples and measuring cells, which are mounted together on a small support which is fixed by fire-proof cement on the free end of the body at the outside of the sampling chamber.

The part of the head extending outside of the pipe may in front of the sampling chamber be encircled at the outside by a small protection tube. This small protection tube is perfectly loose in relation to the aforesaid pipe and may have a greater inside diameter.

The invention also relates to a head which is visibly destined to be used in a sampling device according to one of the aforesaid embodiments.

Other particulars and advantages of the invention will appear from the following description of non-limiting embodiments of sampling devices for liquid metals according to the invention, reference being made to the attached drawings.

FIG. 1 represents an outside view of a sampling device according to the invention.

FIG. 2 represents a section taken along line II—II in FIG. 1.

FIG. 3 represents a section taken along line III—III in FIG. 2.

FIG. 4 represents half a section of a modified embodiment.

FIG. 5 is a view similar to that of FIG. 4, but for still another embodiment.

FIG. 6 represents on a large scale the part which is indicated as F6 in the FIGS. 4 and 5.

FIG. 7 represents a section embodiment line VII—VII in the FIGS. 4 and 5.

FIG. 8 represents a view in perspective of the end of the head which is provided with a sampling device with measuring equipment according to the invention.

FIG. 9 represents on a larger scale a lateral view with partial cut away of the part of the sampling device according to FIG. 8.

FIG. 11 represents a cross section taken along line XI—XI in FIG. 9.

FIG. 12 represents a cross section taken along line XII—XII in FIG. 9, but without cement.

Figure 10:
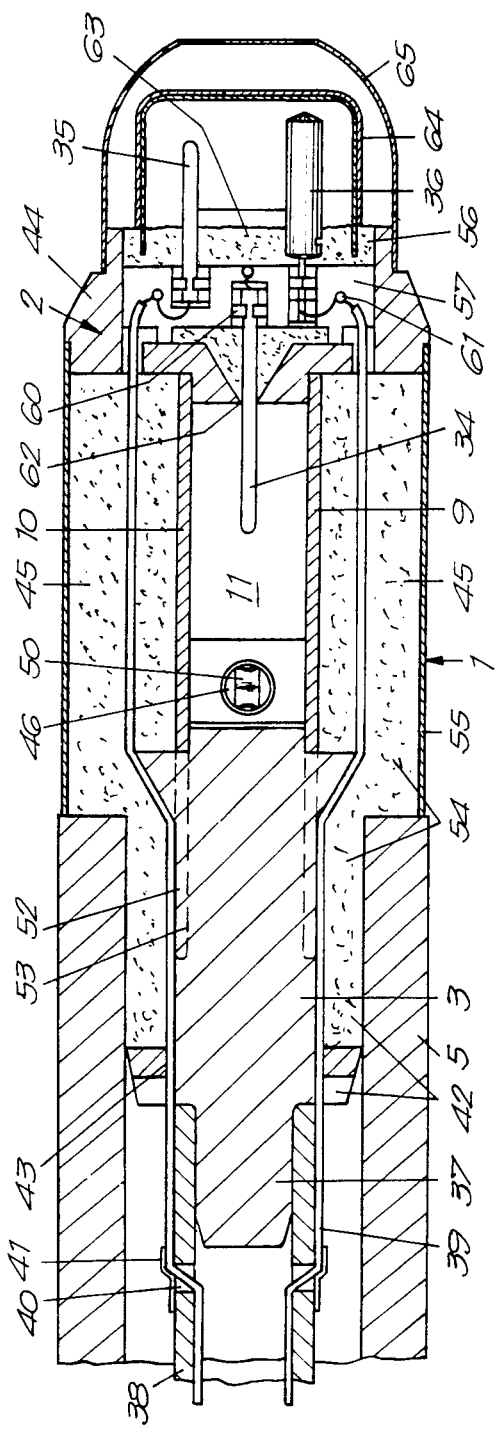
FIG. 10 represents a longitudinal section taken along line X—X in FIG. 9.

As represented in the FIGS. 1 through 3, the device according to the invention mainly consists of a head 1 made of porous fireproof material, for instance moulding sand, this head being externally formed by a part 2 with a large diameter and a part 3 with a smaller diameter, in order in this way to form a collar 4, the purpose of which is to make it possible to fix a suchlike head in an appropriate way of a cardboard tube 5 which does or does not form the carrying lance properly speaking.

Preferably, at least the part 3 is made partially conically in order, with or without the intervention of glue, to ensure the clamping fixation of the head 1 on the pipe 5.

In the part 2 of the aforesaid head 1, two spaces are concentrically provided for, respectively 6 and 7, which are preferably made cylindrical and slightly conical, whereby the smallest diameter of the space 7 is larger than the largest diameter of the space 6 in order so to form a collar 8.

In this way it is possible to place a metal cooling component 9 on the bottom of the space on chamber 6, while on the collar 8 a metal cooling component 10 can be mounted.

The so formed chamber 11 is connected with the outside wall of the head 1 via an inflow orifice which is formed by a part with a smaller diameter 12 and a part with a larger diameter 13 whereby, in the bottom of this part 13 there is provided a metallic retarding screen or closing component 14 which acts in a retarding way on the supply of metal to the chamber 11, while the orifice 13 is also closed by a retarding screen 15, for instance in the form of a small paper disc.

The invention described hereinabove can be extended by providing for, in the part 3 of the head 1, a passage 16 which connects the rear end of the head 1 with the aforesaid chamber 6. After placing the metal cooling component 9 in the head 1, an adhesive, for instance fireproof cement, 17 can be applied in the passage 16 to keep the small plate 9 in its place in the head 1.

Above the metal cooling component 10 a little quartz tube 18 can be provided for, as represented in the drawings, the length of which is equal to the local diameter of the aforesaid space 7. This little quartz pipe 18 being connected to an orifice provided for in the wall of the head 1, formed by a part 19 with a smaller diameter and a part 20 with a larger diameter, whereby in the bottom of the port 20 a retarding screen 21, for instance made of metal, is mounted, the orifice 20 itself being closed by a retarding screen 22, made for instance of paper.

The little pipe 18 will be kept in place in the space 7, more especially in relation to the inflow orifice 19-20, by means of an adhesive applied in the space 7 of the head 1, for instance fireproof cement 23.

It is clear that in this way one obtains a sampling device which is extremely simple as far as the shaping and the components are concerned and whereby operations on the various parts and mounting thereof are very simple and limited to a minimum.

The sampling device according to the invention permits the gases developed during the sampling operation to escape in a simple way through the porous structure pervious to gases of the material of which the head 1 is made directly via the metal bath so that a complete filling of the chamber 11 in order to obtain a disk-shaped sample can be obtained and the little quartz pipe 18 can be completely filled in order to obtain a sample in the shape of a bar.

Another important advantage of the device according to the invention is the flexibility of the same to obtain various sampling devices which distinguish themselves by the thickness of the sample.

It suffices to have the distance of the collar 8 to the bottom of the chamber 6 made in various dimensions, for instance 6 mm, 8 mm and 12 mm.

This can be done quite readily, because to make such different sand moulds, it is only necessary to change the mandrel of the matrix, so that the supplementary costs therefore are very small.

In the FIGS. 4 through 6 there are shown variants which distinguish themselves from the first embodiment in that the head 1 is made of two parts, 24–25 respectively. By this means the small metal cooling plates 9–10 may be fitted from both extremities of part 24. The sampling chamber 11 is defined by the plates 9–10 and the inner rib 26 which forms abutments 27–28 for the aforesaid plates 9–10.

These abutments 27–28 are preferably made a little recessed or conically to prevent the formation of burrs on the sample.

In the FIGS. 4 and 5 there is shown furthermore that the inflow orifice 12 can be closed in a simple way by a little cap 29 which is mounted in a clamping way while a recess 30 is provided for in order to form an easy to break out wall 31 in case a quartz pipe 18 is to be mounted.

On the wall 26 of the chamber 11 protrusions 32 are also provided to impress a mark in the sample to identify the sample.

In FIG. 4 is finally shown the part 25 with the purpose to slide thereover a tube 5, while the part 25 in FIG. 5 is provided with an annular chamber 33 wherein the pipe 5 may be introduced.

In the embodiment according to the FIGS. 9 through 12, a variant is shown whereby the head 1 constitutes also a measuring head. In this embodiment the sampling device consists of a head 1 which is fixed on an end of a round pipe 5. The head 1 mainly consists of a part 2 and of metal cooling plates 9–10 which limit together the sampling chamber and which in this case are located along the longitudinal axis of the head 1. Part 2, as in the previous examples, is made of moulding sand agglomerated with resin, for instance phenol resin, it being possible to effectively agglomerate the sand with the resin at 140° Celsius.

The part 2 is placed with a smaller end 3 in the pipe 5, while the sampling chamber 11 of the part 2 is located outside of the pipe 5.

The embodiment form according to the FIGS. 9 through 12 differs from the embodiment according to the FIGS. 1 to 8 mainly through the other shape of part 2, the little cooling plates 9–10 and the sampling chamber 11 and through the fact that the head 1 contains two thermocouples 34–35 and an oxygen measuring cell 36.

The endmost part 37 of the narrow end 3 is a massive cylinder with a conical end and with a diameter which is smaller than the inside diameter of the pipe 5.

Over this part 37 an inner pipe 38 made of cardboard is pushed which extends coaxially in the pipe 5, whereby in this inner pipe 38 the electric lines 39 are located which connect the thermocouples 34 and 35 and the oxygen measuring cell 36 with the measuring apparatuses properly speaking. These lines 39 which extend along part 3 and enter the inner pipe 38 just past this part 3 through orifices 40 in the inner pipe 38. The orifices are covered by a ring 41.

The narrow end 3 properly speaking is a massive cylinder, the diameter of which is equal to the inside diameter of the pipe 5, but which at the end of the part 37 is slightly conical. On both sides this part 3 is provided along its full length of a recess for an electric line 39, whereby each recess is mainly formed by a gutter 42 turned towards the outside of part 3. The gutter is partly closed on the conical end. At this place, the line 39, which is adjacent to the bottom of the gutter 42, extends through an orifice 43 which is oriented parallel to the axis of the part 3. In this way the line 39 is maintained in place in the recess 42–43.

The pipe 5 is clamped over the part 3 and/or glued to this part and extends as far as against the wider part 44. The wider part 44 is mainly a cylinder the diameter of which is a little smaller than the outside diameter of the pipe 5. However, opposite sides of the part 44 are provided with a recess 45 which is in alignment with the recesses 42–43 in the part 3. Each recess 45 extends parallel to the axis of the part 3 up to a little distance of the free end of the part 2.

The two recesses 45 are connected together with an aperture, extending in a cross direction, which is closed on both sides by a small cooling plate 9–10 and which between these small cooling plates forms the sampling chamber 11.

The small cooling plates 9–10 are placed with their periphery against the corresponding recess 45, around the sampling chamber 11.

Parallel to the small cooling plates 9–10 the sampling chamber 11 has a section which has the shape of a rectangle with rounded-off corners. The chamber is provided with a recess at the end of the chamber adjacent to pipe 5. A supply orifice 46 extends radially from the last-mentioned recess and has a widened end which faces the outside of the part 44 halfway between the recesses 45.

The recess of the sampling chamber 11 from which the supply orifice 46 extends is provided with a metallic lining 47.

A little quartz tube 48 is mounted in the supply orifice 46. The end of the quartz tube in the widened end of the supply orifice 46 is closed by a small metallic cap 49 which keeps in place a small curved metallic plate 50 located in the small quartz tube 48. The ends of the plate 50 are folded over the end of the small quartz tube 48. The small cap 49 has its border bedded in fireproof cement 51 which is applied around the small quartz tube 48 in the bottom of the widened end of the supply orifice 46.

The small cooling plates 9–10 have mainly the shape of a rectangle in which the two corners which are distant from the pipe 5 are rounded off. Two fine tails 52 are formed on the opposite end of the cooling plates. The two tails 52 of each small cooling plate 9–10 extend parallel to each other up to in the pipe 5 and lie sunk down in grooves 53 which are provided for in the bottom of the corresponding recess 45 and in the outside of the part 3.

The small cooling plates 9–10 with their tails 52 are kept in place against the part 2 by means of fireproof cement 54 with which one fills the recesses 45 in the part 44 and the grooves 53 in the part 3. One fills also the recesses 42–43 with cement 54. One uses thereby a round rubber template which one removes after the hardening of the cement 54. The parts 3 and 44 show thereby together with the cement 54 a cylindrical outer surface.

The tails 52 bedded in the cement form an armature which extends into the pipe 5 and reinforces the part 2. Mainly, the breaking off of the wider part 44 located outside of the pipe 5 of the narrow end 3–37 is prevented.

The lines 39 which extend through the recesses 45 and the recesses 42–43 become at the same time bedded in the cement and are kept in place and protected by this cement.

The part 44, excepting a small part at its free end, is surrounded by a small protection sheath 55 which is markedly thinner than the pipe 5 and has an outside diameter which is a little smaller than the outside diameter of the pipe 5.

The end of the wider part 44 runs conically, but has, adjacent to the small protection sheath 55, a greatest diameter which is equal to the outside diameter of the small protection sheath 55 and thus is a little smaller still than the outside diameter of the pipe 5. The last mentioned end is provided with an oblong recess 56 which extends in a direction which is transversal in relation to the small cooling plates 9–10 and which faces the side of the part 2 which is faces away from the pipe 5.

In this recess 56, a small plastic support 57 is provided for on which the thermocouples 34 and 35 and the oxygen measuring cell 36 are fixed.

This small support 57 contains the body 58 in the shape of a lath which has its width direction parallel to the longitudinal axis of the body 1. The body is furthermore provided with fixing projections 60 with which the thermocouples 34–35 and the oxygen measuring cell 36 are fixed on the support. Furthermore, the body 58 is also provided with pins 61 with which the small connection cables of the two thermocouples and of the measuring cell are connected. The electric lines 39 are also connected with these pins 61 in order to make electric contact with the aforesaid small connection cables.

The thermocouple 35 and the oxygen measuring cell 36 are oriented away from the part 2. The thermocouple 34, on the contrary plunges through a small orifice 62 in the sampling chamber 11. This orifice 62 and the complete recess 56 from which it projects are filled with fireproof cement 63. The small support 57 and the ends of the thermocouples 34 and 35 and of the oxygen measuring cell 36 fixed thereon are sunkdown in the cement 63 and are fixed in this way on the part 2.

The parts of the thermocouples 35 and of the oxygen measuring cell 36 protruding above the cement 63 are protected by a metallic cap 64, which is partially pushed in the cement 63 before the hardening of same. Over the cap 64 a second cap 65 is fitted, which is clamped on the end of the part 44.

The head 1 described hereinabove is of a very simple construction. The part 2 can be made in a die in one operation. All other parts of the head 1 can be placed after the part 2 has been manufactured. Among others, the thermocouples 34 and 35, the oxygen measuring cell 36 and the small cooling plates 9–10 are placed afterwards. The mounting of the thermocouples 34 and 35 and of the oxygen measuring cell 36 can take place very rapidly and in a simple way, due to the fact that these components are already fixed on the small support 57.

It suffices to place the latter and then to fill the recess 56 with cement 63.

The fixing of the small cooling plates 9–10 also takes place in a simple way through the use of fireproof cement 54, whereby the small cooling plates also form framework for the head 1 which, not withstanding the fact that the part of the body 2 is made from moulding sand, is relatively solid and keeps a sufficient solidity during the sampling.

Due to the fact that part 2 is made of moulding sand, gases can escape through this body in the course of the sampling. Due to the fact that by the immersion the small protection sheath 55 made from cardboard burns immediately these gases can escape laterally from the body or part 2, in such a way that practically no gases penetrate into the pipe 5.

One thus obtains, as in the embodiments according to FIGS. 1 through 8, a complete filling of the sampling chamber 11 and a sample without gas inclusions.

Due to the fact that the pipe 5 surrounds only a narrow end 3–37 of the body 2 and the wider part 44 with the sampling chamber 11 is located entirely outside of the pipe 5, the diameter of the pipe 5 may be relatively small. Due to this, the pipe 5 is relative cheap and light.

Due to the fact that the sampling chamber 11 is located completely outside of the pipe 5, the releasing of the sample is very easy. It suffices to smash the part of the head 1 protruding outside of the not yet burned down tube 5.

For the sake of completeness it should be noted that the sampling device according to the invention allows in a simple way to use a deoxidizer, such as aluminum, zirconium and titanium, through introducing same in the sampling chamber in the form of foil or wire which may be folded in a zig-zag, or in the inflow aperture as a ring or a little sleeve.

It is clear that the invention is not limited to the invention described as an example and shown in the attached drawings, but that such sampling device can be made in various shapes and dimensions without going outside the frame of the invention.

We claim:

1. A sampling device for molten metals comprising a pipe (5), and a head (1) fixed on the end of the pipe, said head having a sampling chamber (11), said head (1) including a part (2–24) made of fireproof material which partially limits the sampling chamber (11), said part (2) having a supply orifice (12–46) to the sampling chamber (11) and a narrow end (3) protruding into the pipe (5), the sampling chamber (11) being located completely outside of the pipe (5), said head including a small cooling plate (9) forming a part of the wall of the sampling chamber (11), the part (2) being made of a material which has a structure permeable to gases during sampling of the molten metal.

2. The sampling device according to claim 1, wherein the part (2) is made of agglomerated sand.

3. The sampling device according to claim 1 wherein the part (2) of the head (1) is made of one piece.

4. The sampling device according to claim 1, wherein the sampling chamber in the head (1) includes two axially aligned substantially cylindrical spaces (6–7), one of the spaces (7) being located at the immersion end of the head (1) and having a diameter slightly greater than the diameter of the other one of the spaces (6) whereby a collar (8) is formed between the spaces (6–7), said collar supporting a second cooling plate (10), said cooling plates being metallic, and the supply orifice being a radially oriented inflow aperture (12) which communicates with the sampling chamber between the metallic cooling plates (9–10).

5. The sampling device according to claim 1, wherein the sampling chamber in the head includes two axially aligned substantially cylindrical spaces (6–7), one of the spaces (7) being located at the immersion end of the head (1) and having a diameter a little greater than diameter of the other one of the spaces (6) whereby a collar (8) is formed between the spaces (6–7), said collar supporting a second cooling plate (1), said plates being metallic, a quartz tube (18) being located in the one space (7), the length of said quartz tube being at least as great as the diameter of the one space (7), the supply orifice being a radially oriented inflow aperture (12) and the head (1) having a second radially directed inflow aperture (19), one of the apertures communicating with the sampling chamber between the metallic cooling plates (9-10), the second one of the apertures communicating with said quartz (18).

6. The sampling device according to claim 5, wherein the metallic cooling plate (10) is located in the one space (7) and an adhesive matter (23) is applied to maintain the second metallic plate (10) and the quartz tube (18) in place.

7. The sampling device according to claim 4, wherein the other space (6) is lengthened towards the end of the head (1) opposite the immersion end by means of a passage (16), the passage having a diameter less than the diameter of the sampling chamber, whereby an adhesive matter (17) in the passage maintains the first cooling plate (9) in place.

8. The sampling device according to claim 4, wherein the spaces (6-7) are in the shape of trucated cones, the greatest diameter of each truncated cone being adjacent the immersion end of the head (1).

9. The sampling device according to claim 4, wherein the inflow aperture is formed of two parts (12-13) and (19-20) with different diameters, the part (13-20) having the greatest diameter communicating with the outside of the head (1), and a metal closing disk (14-21) is located between the two parts of the aperture.

10. The sampling device according to claim 9, wherein the metal closing disk (14-21) has a diameter which is a little greater than the diameter of the inflow aperture part (13-20) with the greatest diameter (12-19) and is pressed into the inflow aperture with the greatest diameter.

11. The sampling device according to claim 4, wherein the outside end of the inflow aperture (12-19) is closed by a retarding screen (15-22) which is mounted on the exterior wall of the head (1).

12. The sampling device according to claim 1, wherein the outside wall of the heading (1) is formed by the part (2) at the immersion end, and the narrow end (3) opposite the immersion end, the narrow end having a diameter smaller than the diameter of the part at the immersion end, whereby the narrow end may be fixed in the pipe (5).

13. The sampling device according to claim 1, wherein the head includes a second cooling plate (10) and the part (24) has a rib (26) in the sampling chamber which serves as an abutment for the cooling plates (9-10).

14. The sampling device according to claim 13, wherein the second cooling plate (10) is kept in place by fireproof cement and the first cooling plate (9) is kept in place by a part (25) having a projection which projection enters a bore in the ribbed part (24) whereby the first cooling plate is abutted against the rib by the projection.

15. The sampling device according to claim 1, wherein the supply orifice (12) is surrounded by a cavity in the form of a ring in which the edge of a closing cap (29) can be fixed.

16. The sampling device according to claim 1, wherein the head 11 includes a second cooling plate (10) which forms part of the wall of the sampling chamber (11) in the part (2), and the supply orifice (12) communicates with the sampling chamber (11) and the outer side of the part (2) which is located outside of the pipe (5).

17. The sampling device according to claim 1, wherein the head (1) has an armature (52).

18. The sampling device according to claim 17, wherein the armature (52) extends into the narrow end (3) of the head (1) which is located in the pipe (5).

19. The sampling device according to claim 17, wherein the armature (52) forms a part of the cooling plate (9).

20. The sampling device according to claim 1, the head (1) includes a second cooling plate (10), each cooling plate (9-10) forming a lateral wall of the sampling chamber (11) extending along the longitudinal axis of the head (1).

* * * * *